(12) United States Patent
Lin et al.

(10) Patent No.: US 10,487,037 B2
(45) Date of Patent: Nov. 26, 2019

(54) PROCESS FOR PREPARING AN IODINATED FATTY ACID ETHYL ESTER

(71) Applicant: Food Industry Research and Development Institute, Hsinchu (TW)

(72) Inventors: Chih-Chiang Lin, Tainan (TW);
Chih-Hong Tung, Zhubei (TW);
Yan-Hwa Chu, Hsinchu (TW);
Ding-Yuan Su, Hsinchu (TW)

(73) Assignee: Food Industry Research and Development Institute, Hsinchu (TW)

( * ) Notice: Subject to any disclaimer, the term of this patent is extended or adjusted under 35 U.S.C. 154(b) by 0 days.

(21) Appl. No.: 16/031,687

(22) Filed: Jul. 10, 2018

(65) Prior Publication Data

US 2019/0016664 A1   Jan. 17, 2019

(30) Foreign Application Priority Data

Jul. 12, 2017 (TW) .............................. 106123300 A
May 24, 2018 (TW) .............................. 107117730 A

(51) Int. Cl.
| | | |
|---|---|---|
| *C07C 67/287* | (2006.01) | |
| *C11C 3/00* | (2006.01) | |
| *C07C 69/604* | (2006.01) | |
| *C07C 69/65* | (2006.01) | |
| *C07C 67/03* | (2006.01) | |
| *C07C 67/08* | (2006.01) | |
| *C07C 67/02* | (2006.01) | |

(52) U.S. Cl.
CPC .......... *C07C 67/287* (2013.01); *C07C 69/604* (2013.01); *C07C 69/65* (2013.01); *C11C 3/003* (2013.01); *C07C 67/02* (2013.01); *C07C 67/03* (2013.01); *C07C 67/08* (2013.01); *C11C 3/00* (2013.01)

(58) Field of Classification Search
CPC ..... C07C 67/287; C07C 69/604; C07C 69/65; C07C 67/02; C07C 67/03; C07C 67/08; C11C 3/00; C11C 3/003
See application file for complete search history.

(56) References Cited

U.S. PATENT DOCUMENTS 1,870,023 A  *  8/1932  Raiziss ............. A61K 49/0433
                                                    424/9.4
6,124,357 A  *  9/2000  Jung .................... C07C 67/307
                                                    514/546

FOREIGN PATENT DOCUMENTS

| CA | 2164931 | * | 7/1994 | |
| CN | 101245007 A | * | 8/2008 | ............. C07C 67/03 |
| CN | 101676255 | * | 3/2010 | |
| CN | 101676255 A | | 3/2010 | |

(Continued)

OTHER PUBLICATIONS

English translation of CN101676255, Mar. 24, 2010, pp. 1-8 (Year: 2010).*

(Continued)

*Primary Examiner* — Yate' K Cutliff
(74) *Attorney, Agent, or Firm* — Osha Liang LLP

(57) ABSTRACT

A process for preparing an iodinated fatty acid ethyl ester includes steps of subjecting a fatty acid ester to a protonation reaction with phosphoric acid to form a protonated fatty acid ester, and subjecting the protonated fatty acid ester to an iodination reaction with an alkali metal iodide to obtain an iodinated fatty acid ester.

13 Claims, 3 Drawing Sheets

(56) References Cited

FOREIGN PATENT DOCUMENTS

CN  103045373 B   5/2014
EP     0198344 A1 * 10/1986  ............. C07C 67/62

OTHER PUBLICATIONS

Stone et al., "Iodocyclohexane," Organic Syntheses, Coll. vol. 4, p. 543, (1963); vol. 31, p. 66 (1951) (Year: 1951).*
EP 0198344 (A1), Kuhn, W. et al., Stabilized iodine fats and process for their preparation, 1986, English translation, 4 pages (Year: 1986).*
CN 101245007 (A), Jiangbo, X. et al., Process for producing iodination vegetable oil fatty acid ethyl ester, 2008, English translation, 15 pages (Year: 2008).*

* cited by examiner

LIPIODOL            Ex. 3

PROCESS FOR PREPARING AN IODINATED FATTY ACID ETHYL ESTER

CROSS-REFERENCE TO RELATED APPLICATIONS

This application claims priority of Taiwanese Application No. 106123300, filed on Jul. 12, 2017 and priority of Taiwanese Application No. 107117730, filed on May 24, 2018.

FIELD

The disclosure relates to a process for preparing an iodinated fatty acid ethyl ester.

BACKGROUND

Lipiodol produced and marketed by the French company Guerbet is a fatty acid ethyl ester of iodized poppyseed oil that is injected into the body as a radio-opaque contrast agent for outlining and visualizing internal anatomical structures in radiological examinations. For example, Lipiodol has been used as a contrast agent in lymphangiography, hysterosalpingography, and for diagnosing gastric and hepatic lesions.

Due to increased incidence of diseases such as cancer and stroke in recent years, there is an increasing demand for radio-opaque contrast agent such as Lipiodol to be used in radiological examinations for diagnostic purpose. However, Lipiodol is of relatively high cost. Therefore, it is desirable for those skilled in the art to develop an iodinated fatty acid ethyl ester which may be synthesized from inexpensive and easily available edible oil to be used as a substitute for Lipiodol.

CN103045373B discloses a method for preparing iodinated vegetable oil ethyl ester in which vegetable oil and hydrogen iodide gas are subjected to an addition reaction to generate iodinated vegetable oil. The addition reaction is implemented at a temperature of 25° C. for a period ranging from 16 hours to 96 hours.

CN101676255A discloses a synthetic method for preparing iodinated vegetable fatty acid and ester thereof. In the synthetic method, vegetable fatty acid prepared from vegetable oil via saponification and acidification reactions is subjected to an iodination reaction with hydroiodic acid to obtain iodinated vegetable fatty acid. The iodination reaction is implemented at a temperature ranging from 0° C. to 50° C. for a period ranging from 1 hour to 96 hours.

Both of the methods disclosed in the aforesaid prior art have a relatively slow reaction rate, and are thus time-consuming.

SUMMARY

Therefore, an object of the disclosure is to provide a process for preparing an iodinated fatty acid ethyl ester having an enhanced reaction rate.

According to the disclosure, there is provided a process for preparing an iodinated fatty acid ethyl ester which includes steps of:
  a) subjecting a fatty acid ester selected from the group consisting of a fatty acid ethyl ester and a triglyceride to a protonation reaction with phosphoric acid to form a protonated fatty acid ester; and
  b) subjecting the protonated fatty acid ester to an iodination reaction with an alkali metal iodide to obtain an iodinated fatty acid ester.

BRIEF DESCRIPTION OF THE DRAWINGS

Other features and advantages of the disclosure will become apparent in the following detailed description of the embodiment(s) with reference to the accompanying drawings, of which.

DETAILED DESCRIPTION

Figure 1:
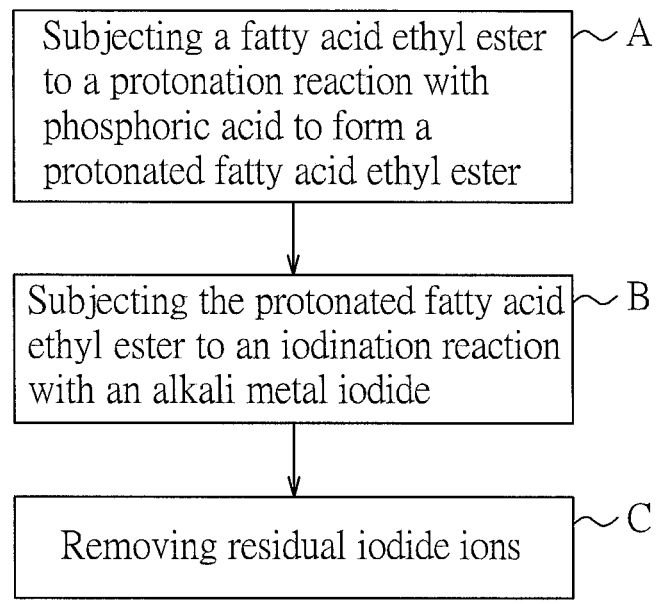
FIG. 1 is a flow diagram of a first embodiment of a process for preparing an iodinated fatty acid ethyl ester according to the disclosure as illustrated by Examples 1-5.

Referring to FIG. 1, a first embodiment of a process for preparing an iodinated fatty acid ethyl ester according to the disclosure includes steps of:
  A) subjecting a fatty acid ethyl ester to a protonation reaction with phosphoric acid to form a protonated fatty acid ethyl ester;
  B) subjecting the protonated fatty acid ethyl ester to an iodination reaction with an alkali metal iodide to obtain the iodinated fatty acid ethyl ester; and
  C) removing residual iodide ions.

In certain embodiments, the fatty acid ethyl ester used in step A) is made by subjecting a vegetable oil and ethanol to a reaction in the presence of a base. Examples of the vegetable oil suitable for the reaction include, but are not limited to, sunflower oil, soybean oil, peanut oil, sesame oil, castor oil, cottonseed oil, rapeseed oil, safflowerseed oil, linseed oil, corn oil, poppyseed oil, walnut oil, *Brucea javanica* oil, canola oil, palm oil, olive oil, coconut oil, rice bran oil, camellia seed oil, wheat germ oil, grapeseed oil, and combinations thereof. Specifically, the fatty acid ethyl ester used in step A) may be obtained by subjecting a triglyceride derived from the vegetable oil to an ethyl esterification.

In certain embodiments, in step A), a molar ratio of the fatty acid ethyl ester to the phosphoric acid is in a range from 0.02 to 0.1. The protonation reaction is implemented under stirring at a temperature of from 25° C. to 80° C. for a period of from 25 minutes to 35 minutes.

Examples of the alkali metal iodide used in step B) include, but are not limited to, potassium iodide, sodium iodide, and a combination thereof. The iodination reaction in step B) is implemented at a temperature of from 25° C. to 80° C. for a period of from 3 hours to 12 hours.

In an exemplary embodiment, a molar ratio of the fatty acid ethyl ester to the alkali metal iodide is in a range from 0.2 to 0.8.

In an exemplary embodiment, a purification step is implemented after step B) so as to remove residual phosphoric acid and residual alkali metal iodide.

Figure 2:
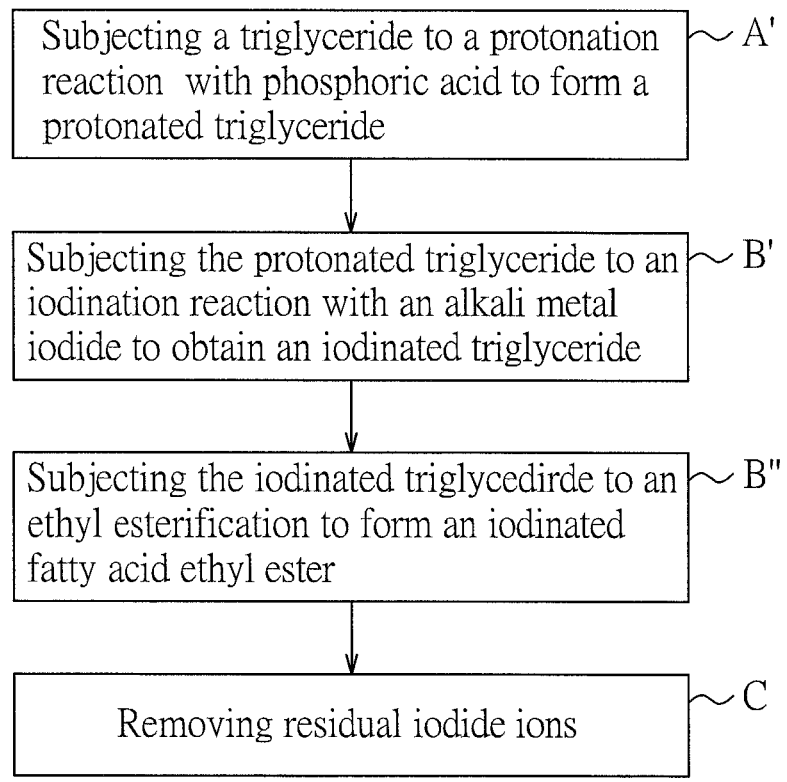
FIG. 2 is a flow diagram of a second embodiment of a process for preparing an iodinated fatty acid ethyl ester according to the disclosure as illustrated by Example 6.

Referring to FIG. 2, a second embodiment of a process for preparing an iodinated fatty acid ethyl ester includes steps of:
  A') subjecting a triglyceride to a protonation reaction with phosphoric acid to form a protonated triglyceride;

B') subjecting the protonated triglyceride to an iodination reaction with an alkali metal iodide to obtain an iodinated triglyceride;

B") subjecting the iodinated triglyceride to an ethyl esterification to form the iodinated fatty acid ethyl ester; and C') removing residual iodide ions.

In certain embodiments, the triglyceride used in step A') is derived from the vegetable oil described above for the first embodiment.

In certain embodiments, in step A'), a molar ratio of the triglyceride to the phosphoric acid is in a range from 0.02 to 0.1. The protonation reaction is implemented under stirring at a temperature of from 25° C. to 80° C. for a period of from 25 minutes to 35 minutes.

Examples of the alkali metal iodide used in step B') include, but are not limited to, potassium iodide, sodium iodide, and a combination thereof. The iodination reaction in step B') is implemented at a temperature of from 25° C. to 80° C. for a period of from 3 hours to 12 hours.

In certain embodiments, a molar ratio of the triglyceride to the alkali metal iodide is in a range from 0.2 to 0.8.

The ethyl esterification in step B") is implemented using ethanol in the presence of a base.

In certain embodiments, a purification step is implemented after step B") so as to remove residual phosphoric acid and residual alkali metal iodide.

The iodinated fatty acid ethyl ester prepared by the method of the disclosure has an iodine content of from 30 wt % to 45 wt % based on a total weight of the iodinated fatty acid ethyl ester.

Examples of the disclosure will be described hereinafter. It is to be understood that these examples are exemplary and explanatory and should not be construed as a limitation to the disclosure.

Preparation Example 1: Preparation of Fatty Acid Ethyl Ester

Refined sunflower oil (100 g, commercially available from Taiwan Sugar Corporation) and sodium hydroxide (4 g) were mixed in ethanol (100 ml, 95 wt %) to form a mixture, followed by a reaction under stirring at a temperature of 60° C. for a period of 1 hour to obtain a crude product.

The crude product was added with n-hexane (200 ml) and distilled water (100 ml) to form an aqueous layer. The aqueous layer was removed by extraction to obtain an n-hexane layer. The n-hexane layer was washed with distilled water to remove residual sodium hydroxide and glycerol, followed by concentration under reduced pressure to remove n-hexane to obtain fatty acid ethyl ester.

Examples 1-5: Preparation of Iodinated Fatty Acid Ethyl Ester from Fatty Acid Ethyl Ester Fatty acid ethyl ester (10 g) of Preparation Example 1 and an aqueous phosphoric acid solution (150 ml, 86.4 wt %, commercially available from J. T. Baker) were mixed under stirring at a temperature listed in Table 1 for 30 minutes to conduct a protonation reaction, thereby obtaining a reaction solution. A molar ratio of fatty acid ethyl ester to phosphoric acid in the aqueous phosphoric acid solution was 0.02.

TABLE 1

| Ex. | Stirring temperature (° C.) |
|---|---|
| 1 | 80 |
| 2 | 80 |
| 3 | 80 |
| 4 | 50 |
| 5 | 25 |

The reaction solution was added with potassium iodide (15 g) in a molar ratio of fatty acid ethyl ester to potassium iodide of 0.53, followed by an iodination reaction at reaction conditions as shown in Table 2, and then adding n-hexane (20 ml) to form an aqueous layer. The aqueous layer containing residual phosphoric acid was removed by extraction to obtain an n-hexane layer. The n-hexane layer was washed with distilled water to remove residual phosphoric acid and potassium iodide in the n-hexane layer, followed by concentration under reduced pressure to remove n-hexane to obtain a crude product.

TABLE 2

| Ex. | Iodination temperature (° C.) | Iodination period (hours) |
|---|---|---|
| 1 | 80 | 12 |
| 2 | 80 | 6 |
| 3 | 80 | 3 |
| 4 | 50 | 3 |
| 5 | 25 | 3 |

The crude product was added with n-hexane (30 ml), sodium hydroxide (2 g), and ethanol (20 ml, 95 wt %), followed by a reaction under stirring at a temperature of 25° C. for a period of 5 minutes and further addition of distilled water (30 ml) to form an aqueous layer. The aqueous layer was removed by extraction to obtain an n-hexane layer. The n-hexane layer was added with an aqueous sodium thiosulfate solution (20 ml, 25 wt %), followed by a reaction under stirring at a temperature of 25° C. for a period of 3 hours to form an aqueous layer. The aqueous layer was removed via extraction to obtain an n-hexane layer. The n-hexane layer was washed with distilled water to remove residual salts in the n-hexane layer, followed by concentration under reduced pressure to remove n-hexane to obtain iodinated fatty acid ethyl ester.

Example 6: Preparation of Iodinated Fatty Acid Ethyl Ester from a Vegetable Oil (A Source of Triglyceride)

Sunflower oil (10 g, containing triglyceride) and an aqueous phosphoric acid solution (50 ml, 86.4 wt %) were mixed by stirring at a temperature of 80° C. for a period of 30 minutes to conduct a protonation reaction, thereby obtaining a reaction solution. A molar ratio of sunflower oil to phosphoric acid in the aqueous phosphoric acid solution was 0.06.

The reaction solution was added with potassium iodide (10 g) in a molar ratio of sunflower oil to potassium iodide of 0.79, followed by an iodination reaction at a temperature of 80° C. fora period of 3 hours, and then addition of n-hexane (20 ml) to form an aqueous layer. The aqueous layer containing residual phosphoric acid was removed by extraction to obtain an n-hexane layer. The n-hexane layer was washed with distilled water to remove residual phosphoric acid and potassium iodide in the n-hexane layer, followed by concentration under reduced pressure to remove n-hexane to obtain an iodinated product containing iodinated triglyceride.

The iodinated product (10 g) was added with sodium hydroxide (0.4 g) and ethanol (100 ml, 95 wt %), followed by a reaction under stirring at a temperature of 60° C. for a period of 1 hour, then adding n-hexane (20 ml) and distilled water (10 ml) to form an aqueous layer. The aqueous layer was removed by extraction to obtain an n-hexane layer. The n-hexane layer was washed with distilled water to remove residual sodium hydroxide and glycerol in the n-hexane layer, followed by concentration under reduced pressure to remove n-hexane to obtain crude iodinated fatty acid ethyl ester.

The crude iodinated fatty acid ethyl ester was added with n-hexane (30 ml), sodium hydroxide (20 g), and ethanol (20 ml, 95 wt %), followed by a reaction under stirring at a temperature of 25° C. for a period of 5 minutes and further addition of distilled water (30 ml) to form an aqueous layer. The aqueous layer was removed by extraction to obtain an n-hexane layer. The n-hexane layer was added with an aqueous sodium thiosulfate solution (20 ml, 25 wt %), followed by a reaction under stirring at a temperature of 25° C. for a period of 3 hours to form an aqueous layer. The aqueous layer was removed by extraction to obtain an n-hexane layer. The n-hexane layer was washed with distilled water to remove residual salts contained in the n-hexane layer, followed by concentration under reduced pressure to remove n-hexane to obtain iodinated fatty acid ethyl ester.

Example 7: Preparation of Iodinated Fatty Acid Ethyl Ester from Fatty Acid Ethyl Ester The procedure of Example 3 was repeated except that potassium iodide used in Example 3 was replaced with sodium iodide (24 g) and that a molar ratio of fatty acid ethyl ester to sodium iodide is 0.42.

Comparative Example 1

The procedure of Example 1 was repeated except that potassium iodide used in Example 1 was replaced with an aqueous hydroiodic acid solution (15 g, 57 wt %).

Comparative Examples 2-4

Fatty acid ethyl ester (10 g) of Preparation Example 1 was added with an aqueous hydroiodic acid solution (10 g, 57 wt %), followed by an iodination reaction under stirring at a temperature shown in Table 3 for a period of 12 hours, followed by adding n-hexane (20 ml) to form an aqueous layer. The aqueous layer was removed by extraction to obtain an n-hexane layer. The n-hexane layer was washed with distilled water to remove residual hydroiodic acid in the n-hexane layer, followed by concentration under reduced pressure to remove n-hexane to obtain a crude product of iodinated fatty acid ethyl ester.

TABLE 3

| Comp. Ex. | Iodination temperature (° C.) |
|---|---|
| 2 | 25 |
| 3 | 50 |
| 4 | 80 |

The crude product was added with n-hexane (30 ml), sodium hydroxide (2 g), and ethanol (20 ml, 95 wt %), followed by a reaction under stirring at a temperature of 25° C. for a period of 5 minutes, followed by addition of distilled water (30 ml) to form an aqueous layer. The aqueous layer was removed by extraction to obtain an n-hexane layer. The n-hexane layer was added with an aqueous sodium thiosulfate solution (20 ml, 25 wt %), followed by a reaction under stirring at a temperature of 25° C. for a period of 3 hours to form an aqueous layer. The aqueous layer was removed by extraction to obtain an n-hexane layer. The n-hexane layer was washed with distilled water to remove residual salts in the n-hexane layer, followed by concentration under reduced pressure to remove n-hexane to obtain iodinated fatty acid ethyl ester.

Methods of Analysis and Measurement

1. X-ray density and X-ray photography:

X-ray photography of each of Lipiodol and the iodinated fatty acid ethyl esters obtained in Examples 1-7 and Comparative Examples 1-4 was carried out in National Cheng Hung University Hospital, Taiwan. X-ray density of the iodinated fatty acid ethyl ester obtained in each of Examples 1-7 and Comparative Examples 1-4 was quantified using ImageJ software developed by the National Institutes of Health, USA.

2. Iodine content:

Iodine content of each of Lipiodol and the iodinated fatty acid ethyl esters obtained in each of Examples 1-7 and Comparative Examples 1-4 was measured according to an iodine content measurement method as described in *Chinese Pharmacopoeia* (2015 edition):1464-1465.

3. Free iodine content:

Free iodine content of each of Lipiodol and the iodinated fatty acid ethyl esters obtained in Examples 1-7 and Comparative Examples 1-4 was measured according to a free iodine content measurement method as described in *Chinese Pharmacopoeia* (2015 edition):1464-1465.

4. Viscosity:

Viscosity of each of Lipiodol and the iodinated fatty acid ethyl esters obtained in Examples 1-7 and Comparative Examples 1-4 was measured at a shear rate of 100 1/s and at a temperature of 20° C. using Thermo Scientific HAAKE RheoStress RS 1500 rheometer.

The X-ray density, iodine content, free iodine content, and viscosity measurement results of Lipiodol and the iodinated fatty acid ethyl esters of Examples 3, 6, and 7 are shown in Table 4. X-ray photographs of the iodinated fatty acid ethyl ester of Example 3 and Lipiodol are shown in FIG. 3.

TABLE 4

|  | Lipiodol | Ex. 3 | Ex. 6 | Ex. 7 |
|---|---|---|---|---|
| X-ray density$^a$ (%) | 100 | 94.9 | — | — |
| Iodine content (wt %) | 37.4 | 36.8 | 36.5 | 35.57 |
| Free iodine content (wt %) | 0.05 | 0.04 | 0.04 | — |
| Viscosity (mPa · s, 20° C.) | 61.9 | 60.4 | 60.1 | — |

Figure 3:
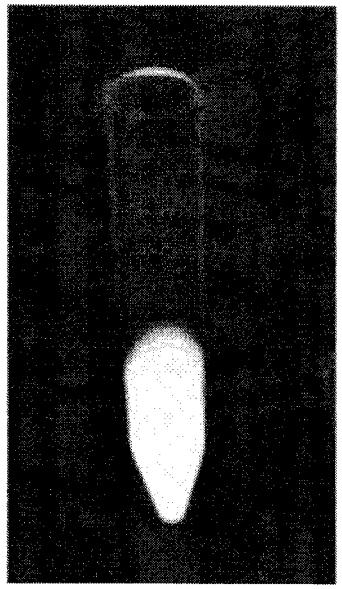
FIG. 3 illustrates X-ray photographs of commercially available Lipiodol and an iodinated fatty acid ethyl ester of Example 3.
Figure 3:
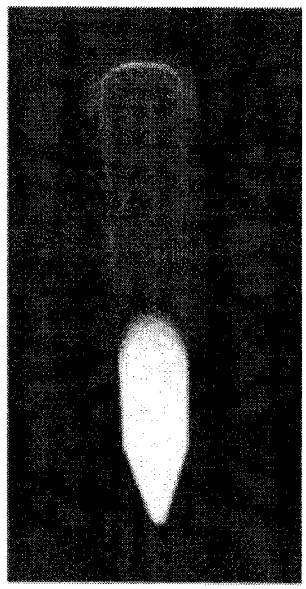

$^a$a ratio of the X-ray density of the iodinated fatty acid ethyl ester to that of Lipiodol As shown in Table 4 and FIG. 3, the iodinated fatty acid ethyl esters of Examples 3, 6, and 7 have physicochemical properties similar to those of Lipiodol.

It should be noted that the iodinated fatty acid ethyl esters of Examples 3, 6, and 7 can be obtained by the iodination reaction implemented at a temperature of 80° C. for a relatively short period of 3 hours.

The iodine content of the iodinated fatty acid ethyl esters of Example 1 and Comparative Example 1 are shown in Table 5.

TABLE 5

|  | Ex. 1 | Comp. Ex. 1 |
|---|---|---|
| Reactant | Potassium Iodide | Hydroiodic acid |
| Iodine content (wt %) | 41.7 | 22.8 |

As shown in Table 5, the iodine content of the iodinated fatty acid ethyl ester of Example 1 is significantly higher than that of the iodinated fatty acid ethyl ester of Comparative Example 1 in which the iodination reaction was implemented using similar reaction conditions as those of Example 1, except that potassium iodide used in Example 1 was replaced with the aqueous hydroiodic acid solution. Therefore, it is demonstrated that the process for preparing an iodinated fatty acid ethyl ester according to the disclosure has a relatively high reaction rate.

The iodine content of the iodinated fatty acid ethyl esters of Examples 1-3 and the iodination period of Example 1-3 are shown in Table 6.

TABLE 6

| Ex. | 1 | 2 | 3 |
|---|---|---|---|
| Iodination period (hours) | 12 | 6 | 3 |
| Iodine content (wt %) | 41.7 | 37.7 | 36.8 |

As shown in Table 6, the longer the iodination period, the higher the iodine content of the iodinated fatty acid ethyl ester.

The iodine content of the iodinated fatty acid ethyl esters of Examples 3-5 and the iodination temperature of Example 3-5 are shown in Table 7.

TABLE 7

| Ex. | 3 | 4 | 5 |
|---|---|---|---|
| Iodination temperature (° C.) | 80 | 50 | 25 |
| Iodine content (wt %) | 36.8 | 36.2 | 33.3 |

As shown in Table 7, the higher the iodination temperature, the higher the iodine content of the iodinated fatty acid ethyl ester.

The iodine content of the iodinated fatty acid ethyl esters of Example 1 and Comparative Examples 2-4 and the iodination temperatures of Example 1 and Comparative Examples 2-4 are shown in Table 8.

TABLE 8

|  | Comp. Ex. 2 | Comp. Ex. 3 | Comp. Ex. 4 | Ex. 1 |
|---|---|---|---|---|
| Iodination temperature (° C.) | 25 | 50 | 80 | 80 |
| Iodine content (wt %) | 2.8 | 6.2 | 11.3 | 41.7 |

As shown in Table 8, the iodine content of the iodinated fatty acid ethyl esters of Comparative Examples 2-4 are significantly lower than that of the iodinated fatty acid ethyl ester of Example 1. Specifically, the iodine content of the iodinated fatty acid ethyl ester of Example 1 is significantly higher than that of the iodinated fatty acid ethyl ester of Comparative Example 4 in which the iodination reaction was implemented using similar reaction conditions as those of Example 1, except that potassium iodide used in Example 1 was replaced with the aqueous hydroiodic acid solution and that in Comparative Example 4, the protonation reaction was not implemented prior to the iodination reaction.

It should be noted that surprisingly, when other monoprotic acids such as acetic acid and p-toluene sulfonic acid, diprotic acids such as oxalic acid, and triprotic acids such as citric acid are used, the protonation reaction cannot be implemented. Specifically, when these protic acids are used, the iodide ions of the alkali metal iodide are oxidized by these protic acids to iodine such that the subsequent iodination reaction cannot be implemented.

In view of the aforesaid, in the process for preparing the iodinated fatty acid ethyl ester according to this disclosure, the fatty acid ester (i.e., the fatty acid ethyl ester or the triglyceride) is first subjected to the protonation reaction with phosphoric acid, which is the source of hydrogen ions, to form a protonated fatty acid ester, and the protonated fatty acid ester is then subjected to the iodination reaction with the alkali metal iodide, which is the source of iodide ions, such that the reaction rate of the process is enhanced.

In contrast, in the process for preparing the iodinated fatty acid ethyl ester of the aforesaid prior art, the iodination reaction is implemented using the hydrogen iodide gas or the hydroiodic acid, which is the source of both the hydrogen ions and the iodide ions, and thus the react ion rate thereof may be unsatisfactory.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A process for preparing an iodinated fatty acid ethyl ester, comprising steps of:
    a) subjecting a fatty acid ester selected from the group consisting of a fatty acid ethyl ester and a triglyceride to a protonation reaction with phosphoric acid to form a protonated fatty acid ester; and
    b) after step a), subjecting the protonated fatty acid ester to an iodination reaction with an alkali metal iodide to obtain an iodinated fatty acid ester.

2. The process according to claim 1, wherein the fatty acid ester in step a) is a fatty acid ethyl ester, and the iodinated fatty acid ester is the iodinated fatty acid ethyl ester.

3. The process according to claim 1, wherein the fatty acid ester in step a) is the triglyceride and the iodinated fatty acid ester obtain in step b) is a iodinated triglyceride, and further comprising, after step b), a step of subjecting the iodinated triglyceride to an ethyl esterification to form the iodinated fatty acid ethyl ester.

4. The process according to claim 1, wherein the protonation reaction in step a) is implemented at a temperature of from 25° C. to 80° C.

5. The process according to claim 1, wherein the protonation reaction in step a) is implemented for a period of from 25 minutes to 35 minutes.

6. The process according to claim 1, wherein the iodination reaction in step b) is implemented at a temperature of from 25° C. to 80° C.

7. The process according to claim 1, wherein the iodination reaction in step b) is implemented for a period of from 3 hours to 12 hours.

8. The process according to claim 1, wherein the triglyceride is derived from a vegetable oil.

9. The process according to claim 1, wherein the fatty acid ethyl ester is made by subjecting a vegetable oil and ethanol to a reaction in the presence of a base.

10. The process according to claim 1, wherein the alkali metal iodide is selected from the group consisting of potassium iodide, sodium iodide, and a combination thereof.

11. The process according to claim 1, wherein a molar ratio of the fatty acid ester to the phosphoric acid is in a range from 0.02 to 0.1.

12. The process according to claim 1, wherein a molar ratio of the fatty acid ester to the alkali metal iodide is in a range from 0.2 to 0.8.

13. The process according to claim 1, wherein the protonation reaction is implemented under stirring.

* * * * *